United States Patent
Hidaka et al.

(10) Patent No.: US 7,601,760 B2
(45) Date of Patent: Oct. 13, 2009

(54) METHOD OF DECOMPOSING PLASTIC

(75) Inventors: Masaru Hidaka, Nara (JP); Takaharu Nakagawa, Ikoma-gun (JP); Toyoyuki Urabe, Ikeda (JP); Tetsuya Maekawa, Amagasaki (JP)

(73) Assignees: Matsushita Electric Works, Ltd., Kadoma-shi (JP); International Center for Environmental Technology Transfer, Yokkaichi-shi (JP)

( * ) Notice: Subject to any disclaimer, the term of this patent is extended or adjusted under 35 U.S.C. 154(b) by 174 days.

(21) Appl. No.: 10/593,081

(22) PCT Filed: Mar. 24, 2005

(86) PCT No.: PCT/JP2005/005366

§ 371 (c)(1),
(2), (4) Date: Sep. 15, 2006

(87) PCT Pub. No.: WO2005/092962

PCT Pub. Date: Oct. 6, 2005

(65) Prior Publication Data

US 2007/0197669 A1    Aug. 23, 2007

(30) Foreign Application Priority Data

Mar. 26, 2004  (JP) .............................. 2004-093363

(51) Int. Cl.
*C08J 11/04*    (2006.01)
(52) U.S. Cl. .......................... 521/48; 521/45; 521/43.5; 521/41; 521/40
(58) Field of Classification Search .................. 521/48, 521/40, 48.5, 41, 43.5, 44, 45; 528/208, 528/272, 301, 488, 328, 290, 256, 182, 90, 528/480, 308.4
See application file for complete search history.

(56) References Cited

U.S. PATENT DOCUMENTS

2006/0247465 A1    11/2006  Hidaka et al.

FOREIGN PATENT DOCUMENTS

| JP | 8 85736 | | 4/1996 |
| JP | 10 24274 | | 1/1998 |
| JP | 10-024274 | * | 1/1998 |
| JP | 11 140224 | | 5/1999 |
| JP | 2000 53801 | | 2/2000 |
| JP | 2002 226871 | | 8/2002 |
| JP | 2004 155964 | | 6/2004 |
| WO | 2004 041917 | | 5/2004 |

OTHER PUBLICATIONS

U.S. Appl. No. 10/593,081, filed Sep. 15, 2006, Hidaka, et al.

* cited by examiner

*Primary Examiner*—James Seidleck
*Assistant Examiner*—Frances Tischler
(74) *Attorney, Agent, or Firm*—Oblon, Spivak, McClelland, Maier & Neustadt, L.L.P.

(57) ABSTRACT

The present invention provides a method for decomposing a plastic so as to recycle useful substances therefrom as raw materials for a similar plastic. In particular, the present invention provides a method for decomposing a plastic, comprising the step of treating a thermosetting resin comprising a polyester and its crosslinking moiety, with subcritical water of a temperature lower than the thermal decomposition temperature of the thermosetting resin. According to the present invention, the thermosetting resin can be decomposed into a polyhydric alcohol, a polybasic acid and a compound comprising an acid residue derived from the polyester and a residue derived from the crosslinking moiety, without causing a random decomposition of the thermosetting resin.

2 Claims, 2 Drawing Sheets

[Figure 1]
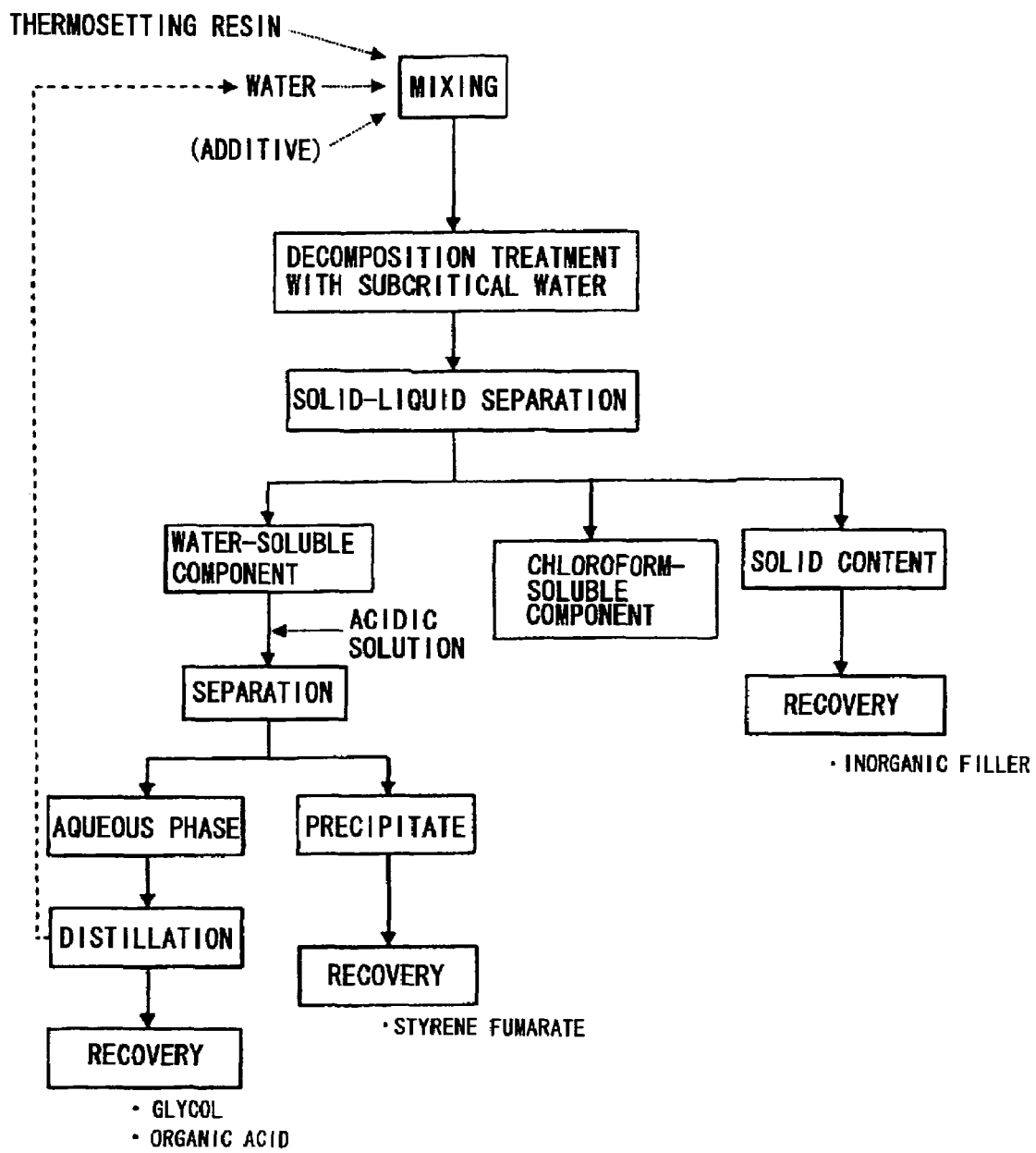

[Figure 2]
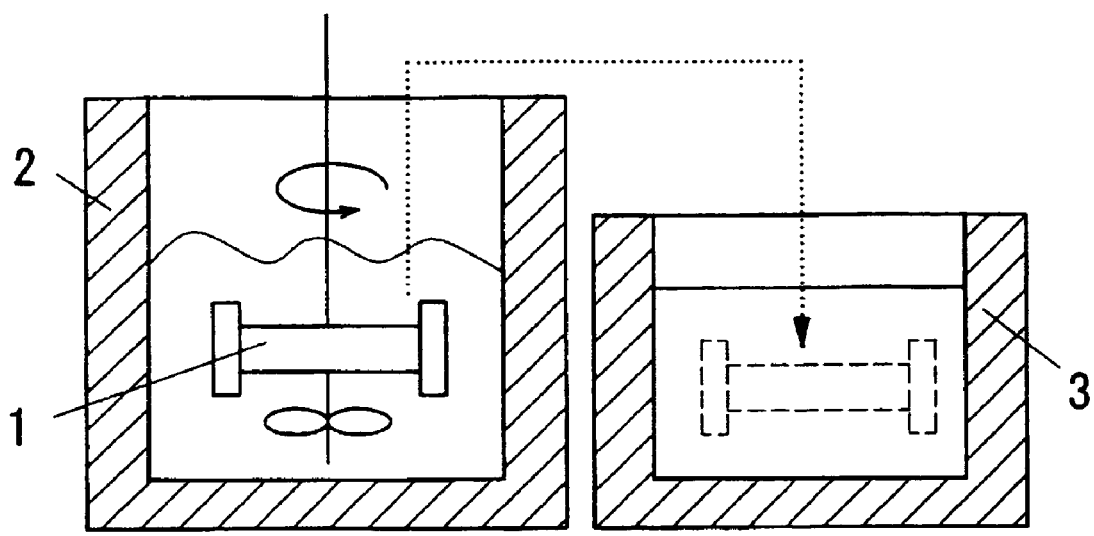
[Figure 3]
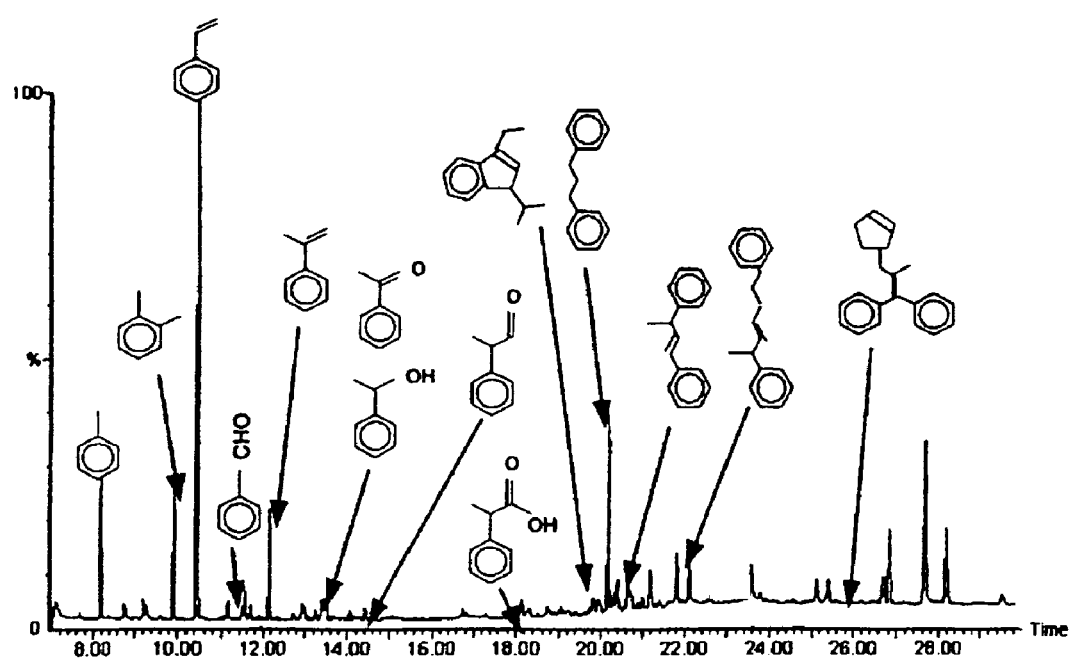

METHOD OF DECOMPOSING PLASTIC

TECHNICAL FIELD

The present application was filed claiming the priority of the Japanese Patent Application No. 2004-093363, the entire contents of which are herein incorporated by the reference.

The present invention relates to a method for decomposing plastics, particularly waste plastics, so as to recover useful substances therefrom.

BACKGROUND OF THE INVENTION

Most of waste plastics hitherto have been dumped by reclaiming lands with the same or incinerating the same, and have never been used as a useful resource. This waste disposal by way of reclaiming the lands has difficulties in the ensuring of sites to be reclaimed and in stable hardening of such sites. On the other hand, the disposal by way of incinerating the waste plastics has disadvantages such as the damage of incinerators, generation of harmful gases and offensive odors, and discharge of $CO_2$. To solve these problems, the Containers and Packaging Recycling Law was instituted in 1995 in Japan, so as to obligate the recovering and recycling of plastics. This trend of recovering and recycling products containing plastics is prevailing in association with the enforcement of a variety of recycling laws.

Under these situations, recently, trials to recycle waste plastics for use as a resource have been attempted. As one of such trials, there is proposed a method of recovering useful oily substances from waste plastics by decomposing the waste plastics through a reaction using supercritical water as a reaction medium. There is also proposed a method of recycling fiber-reinforced plastics used in various structural materials, in which the plastic components in such materials are decomposed by using supercritical water or subcritical water, so as to recover fibers such as glass fibers and carbon fibers for recycling them (cf. Patent Literatures 1 and 2).

By these methods, plastics are decomposed into oily components having lower molecular weights so as to recycle these components as liquid fuels. There is further proposed a method of decomposing plastics, which makes use of a hydrolysis reaction by high temperature water vapor. According to this method, it is possible to decompose the organic polymer components of thermoplastic and thermosetting plastics to some extents.

However, the above methods have a disadvantage in that, since plastics are decomposed in random, the decomposition products are oily materials comprising various components, and thus in that it is difficult to obtain decomposition products with constant qualities. Consequently, a post-treatment for reforming the oily materials by using a catalyst, typically, zeolite, is needed, which results in higher cost. Further, it is difficult to produce petroleum products such as lamp oil and light oil from such reformed oils, and therefore, such reformed oils have not yet been put into practical use. In contemplation of a whole of the global environmental problems such as the exhaust of the petroleum resources and the global warming due to carbon dioxide, drastic countermeasures to decompose and recycle plastics are today unavoidably needed.

Patent Literature 1: JP-A-8-85736 (1996)
Patent Literature 2: JP-A-2000-53801 (2000)

DISCLOSURE OF THE INVENTION

Under the above-discussed circumstances, the present invention is accomplished, and an object of the present invention is to provide a method for decomposing plastics to thereby recycle the decomposition products as raw materials for plastics.

Means for Solving the Problems

A method of the present invention is characterized in that a thermosetting resin comprising a polyester and its crosslinking moiety is treated with subcritical water of a temperature lower than the thermal decomposition temperature of the thermosetting resin.

According to the present invention, a thermosetting resin (or plastic) comprising a polyester and its crosslinking moiety is treated with subcritical water of a temperature lower than the thermal decomposition temperature of the thermosetting resin, to thereby decompose the thermosetting resin into useful substances such as a polyhydric alcohol, a polybasic acid and a compound comprising an acid residue derived from the polyester and a residue derived from the crosslinking moiety, without causing a random decomposition thereof. Further, this method makes it possible to prevent the formation of a decomposition product which is an oily material comprising a plurality of components, and to thereby provide a decomposition product with a constant quality. Furthermore, the resultant decomposition product can be recycled as a raw material for plastics. Particularly, the compound comprising an acid residue derived from the polyester and a residue derived from the crosslinking moiety can be used as not only a raw material for a thermosetting resin but also a low shrinking agent when added to other resin, or a surfactant or a dispersant for pigments in inks.

In the present invention, it is preferable that the subcritical water contains an alkaline salt (preferably, a hydroxide of an alkaline metal).

In this case, the time required for treating the thermosetting resin can be reduced, since the hydrolysis reaction of the thermosetting resin is facilitated. In addition, an organic acid produced by the treatment of the thermosetting resin with the subcritical water can be neutralized with the base of the alkaline salt, so that the secondary decomposition of a concurrently-produced polyhydric alcohol caused by an acid catalytic effect of the organic acid can be inhibited, which leads to an efficient recovery of the polyhydric alcohol.

Preferably, the content of the alkaline salt is not less than 2 molar equivalents relative to the theoretical number of moles of an acid residue contained in a compound comprising the acid residue derived from the polyester and a residue derived from the crosslinking moiety, which is obtained by decomposing the thermosetting resin.

In this case, the organic acid can be sufficiently neutralized and thus can exhibit a higher effect of inhibiting the secondary decomposition of the polyhydric alcohol caused by the organic acid. Furthermore, the compound comprising an acid residue derived from the polyester and a residue derived from the crosslinking moiety can be obtained in higher yield.

Preferably, the plastic-decomposing method of the present invention includes a step of recovering a compound comprising an acid residue derived from the polyester and a residue derived from the crosslinking moiety, obtained by decomposing the thermosetting resin with the subcritical water as mentioned above.

In this case, the compound comprising an acid residue derived from the polyester and a residue derived from the crosslinking moiety can be recycled.

Effect of the Invention

According to the present invention, a thermosetting resin comprising a polyester and its crosslinking moiety can be decomposed into useful substances, i.e., a polyhydric alcohol, a polybasic acid and a compound comprising an acid residue derived from the polyester and a residue derived from the crosslinking moiety, without causing a random decomposition thereof. In other words, decomposition products with constant qualities can be obtained by preventing the formation of a decomposition product which is an oily material comprising a plurality of components. The resultant decomposition products can be recycled as raw materials for plastics, etc.

BRIEF DESCRIPTION OF THE DRAWINGS

FIG. 1 shows a flowchart illustrating a method of the present invention.

FIG. 2 shows a schematic diagram illustrating the step of an Example of the present invention.

FIG. 3 shows a chart illustrating the results of the analysis of a chloroform solution in Comparative Example 1.

BEST MODES FOR CARRYING OUT THE INVENTION

Hereinafter, the best modes for carrying out the present invention will be described.

Plastics to be decomposed in the present invention are thermosetting plastics comprising polyesters and their crosslinking moieties.

The term "polyester" herein referred to means a polymer which is obtained by polycondensation of a polyhydric alcohol component and a polybasic acid component so that polyhydric alcohol residues and polybasic acid residues are linked to each other through ester bonds. There is no particular limit in selection of the polymer, in so far as the object of the present invention can be achieved. The polyester may contain a double bond derived from, for example, an unsaturated polybasic acid.

The term "crosslinking moiety" means a moiety which crosslinks the molecules of the polyester. The crosslinking moiety is, for example, a moiety derived from a crosslinking agent, although not particularly limited thereto. The crosslinking moiety may be a moiety derived from one molecule of crosslinking agent or derived from an oligomer or a polymer (hereinafter collectively referred to as a "polymer") formed by polymerizing a plurality of crosslinking agents. Further, the position and manner of bonding between the molecules and the polyester are not particularly limited.

Accordingly, the "thermosetting resin comprising a polyester and its crosslinking moiety" is a network thermosetting polymer (or a network polyester resin) which is prepared by crosslinking a polyester obtained from a polyhydric alcohol component and a polybasic acid component, through a crosslinking moiety. The resin may be of any type, in so far as the object of the present invention can be achieved. In other words, there is no limit in selection of the type, structure and components of the resin, the type, amount and crosslinking degree of the crosslinking moiety (or a crosslinking agent), and the types and amounts of additives. Preferable as the resin to be used in the present invention is a network polyester resin obtained by crosslinking an unsaturated polyester comprising a polyhydric alcohol and an unsaturated polybasic acid, with a crosslinking agent.

In this connection, the "thermosetting resin" to be used in the present invention mainly means a resin which is cured (or crosslinked) by heating or the like. However, the scope of the resin of the present invention includes an uncured or partially cured resin of which the curing (or crosslinking) is proceeding by heating or the like, in so far as the object of the present invention can be achieved.

Examples of the polyhydric alcohol include, but not limited to, glycols such as ethylene glycol, propylene glycol, diethylene glycol and dipropylene glycol. Each of these glycols may be used in combination.

Examples of the polybasic acid include, but not limited to, aliphatic unsaturated polybasic acids (e.g. aliphatic unsaturated dibasic acids such as maleic anhydride, maleic acid and fumaric acid). Each of the unsaturated polybasic acids may be used in combination with a saturated polybasic acid such as phthalic anhydride or the like.

Examples of the crosslinking agent include, but not limited to, polymerizable vinyl monomers such as styrene and methyl methacrylate.

The present invention is characterized in that the above thermosetting resin is treated with subcritical water (water in a subcritical state) of a temperature lower than the decomposition temperature of the thermosetting resin. This is described in detail: water is added to the above thermosetting resin (mainly the waste of thermosetting plastics), which is then decomposed while the temperature and pressure of water are being increased to put the water in a subcritical state. By doing so, monomers (a polyhydric alcohol and a polybasic acid) derived from the polyester and a compound comprising an acid residue derived from the polyester and a residue derived from the crosslinking moiety can be recovered.

The "compound comprising an acid residue derived from the polyester and a residue derived from the crosslinking moiety" herein referred to is a reaction product obtained by the reaction between the polybasic acid and the crosslinking moiety caused by the hydrolysis of the polyester. The acid residue includes a residue derived from a polymer formed by the polymerization of the above polybasic acid. For example, when the polyester contains a fumaric acid residue and the crosslinking moiety is a styrene polymer, a styrene-fumaric acid copolymer is obtained as the above-mentioned compound.

The ratio of the thermosetting resin to water is not particularly limited. Preferably, 100 to 500 parts by weight of water is added to 100 parts by weight of the thermosetting resin.

The "subcritical water" referred to in the present invention means water in such a state that the temperature and pressure of the water are within the following ranges, respectively: the temperature and the pressure of water are not higher than the critical points of water (critical temperature: 374.4° C., and critical pressure: 22.1 MPa), provided that the temperature of the water is concurrently not lower than 140° C. (in this temperature range, the ionic product becomes about 100 times larger than that found at a room temperature, and the dielectric constant of the water becomes about 50% lower than that found at a room temperature, so that the hydrolysis of the thermosetting resin is facilitated to decompose it into monomers), and provided that the pressure of the water is concurrently not lower than 0.36 MPa (i.e. a saturated vapor pressure at 140° C.).

The temperature of the subcritical water in the present invention is lower than the thermal decomposition temperature of the thermosetting resin, preferably from 180 to 270° C. When the temperature of the subcritical water is lower than 180° C. during the decomposition reaction, a very long time is required to decompose the thermosetting resin, which may lead to a higher cost. On the other hand, when the temperature of the subcritical water is higher than 270° C. during the decomposition reaction, the polyester and the crosslinking moiety are decomposed, which makes it hard to recover a compound comprising an acid residue derived from the polyester and a residue derived from the crosslinking moiety.

The thermal decomposition temperature of the thermosetting resin means a temperature which corresponds to the intersection point of a tangent drawn at a bending point of the decomposition steps of a resin component on a chart obtained by the thermogravimetric analysis (or TG analysis) of a resin sample, with a zero horizontal line of the TG curve.

The treating time for the thermosetting resin by using the subcritical water changes depending on the conditions such as the reaction temperature, etc. Preferably, the treating time is from about 1 to about 4 hours. The better, the shorter the treating time is, since the cost for treating is reduced. The pressure during the decomposition reaction (the treatment with the subcritical water) changes depending on the conditions such as the reaction temperature, etc. Preferably, the pressure is from about 2 to about 15 MPa.

In general, the decomposition of plastics by using subcritical water is caused by thermal decomposition and hydrolysis of the same. This decomposition is similarly caused in a thermosetting plastic (or resin) which is manufactured from a raw material containing a polyhydric alcohol and an organic acid. However, in the present invention, the foregoing thermosetting resin is allowed to contact the subcritical water of a temperature lower than the thermal decomposition temperature of the resin, to thereby selectively cause a hydrolysis reaction. As a result, useful substances, that is, a polyhydric alcohol, a polybasic acid and a compound comprising an acid residue derived from a polyester and a residue derived from a crosslinking moiety can be obtained. These decomposition products can be recovered and recycled as raw materials for plastics, etc.

It is preferable in the present invention that the subcritical water contains an alkaline salt. The alkaline salt in the subcritical water accelerates the hydrolysis reaction of the thermosetting resin, so that the treating time and cost can be saved. When the thermosetting resin is treated with subcritical water within a high temperature range close to a supercritical state, a polyhydric alcohol as one of the decomposition products may be subjected to a secondary decomposition due to the acid catalytic effect of an organic acid which is concurrently produced. When an alkaline salt is contained in subcritical water, the base of the alkaline salt can neutralize the organic acid to thereby inhibit the above secondary decomposition of the polyhydric alcohol.

The term "alkaline salt" means a salt of an alkaline metal or a salt of an alkaline earth metal, which reacts with an acid to show basic properties. Examples of the alkaline salt include, but not limited to, the hydroxides of alkaline metals such as potassium hydroxide (KOH), sodium hydroxide (NaOH), etc., calcium carbonate, barium carbonate, calcium hydroxide, magnesium carbonate, etc., among which the hydroxides of the alkaline metals are particularly preferable.

Although not particularly limited, the content of the alkaline salt in the subcritical water is preferably not less than 2 molar equivalents relative to the theoretical number of moles of an acid residue contained in a compound comprising the acid residue derived from the polyester and a residue derived from the crosslinking moiety, which is obtained by decomposing the thermosetting resin. When the content of the alkaline salt is less than 2 molar equivalents, it may become hard to recover the above compound. While not limited to, the upper limit of the content of the alkaline salt in the subcritical water is preferably not more than 10 molar equivalents in view of cost.

The "theoretical number of moles of an acid residue contained in a compound comprising the acid residue derived from the polyester and a residue derived from the crosslinking moiety" means an estimated number of moles of the acid residue in the compound obtained through the decomposition calculated from a ratio of the number of the molecules of the acid residue and the number of the molecules of the residue derived from the crosslinking moiety, obtained by the NMR analysis of the compound, and from the amount of the crosslinking moiety-forming material used.

Hereinafter, the present invention will be described in more detail with reference to FIG. 1.

FIG. 1 shows a flowchart illustrating the steps of decomposing a thermosetting resin which comprises a polyester and its crosslinking moiety, by using subcritical water; and recovering a polyhydric alcohol, a polybasic acid, a compound comprising an acid residue derived from the polyester and a residue derived from the crosslinking moiety, and an inorganic filler contained in the resin.

Firstly, the thermosetting resin to be treated and decomposed, water and additives such as a hydroxide of an alkaline metal, etc. are mixed, and the mixture is heated and pressurized so that the thermosetting resin is decomposed with subcritical water of a temperature lower than the decomposition temperature of the thermosetting resin. Next, the decomposition products are cooled and are then separated into the solid and liquid contents by filtration or the like. In this step, the inorganic fillers in the thermosetting resin, such as glass fibers and calcium carbonate, are obtained as the solid contents, and water and the water-soluble components dissolved in the water are obtained as the liquid contents. If necessary, the solid content may be mixed with a solvent such as chloroform or the like, when the solid content contain non-reacted residue of the thermosetting resin. By doing so, a component soluble in the solvent (i.e. the non-reacted residue of the thermosetting resin) and an inorganic filler insoluble in the solvent can be separated from each other. As a result, the inorganic filler with high purity can be recovered.

On the other hand, an acidic solution such as hydrochloric acid or the like is added to the liquid content obtained by the above solid-liquid separation to thereby neutralize or acidify the liquid content so as to form a precipitate. Then, such a liquid content is separated into an aqueous phase and the precipitate by filtration or the like. The precipitate is recovered to obtain a compound comprising an acid residue derived from the polyester and a residue derived from the crosslinking moiety (e.g. a styrene-fumaric acid copolymer (styrene fumarate) or a styrene-maleic acid copolymer). The resultant styrene fumarate or the like can be added to other resin so as to be recycled as a low shrinking agent, a surfactant or a dispersant for pigments in ink. In the meantime, the aqueous phase may be distilled to thereby separately recover water, a polyhydric alcohol such as glycol and an organic acid. These materials can be recycled as raw materials (monomers) for plastics. The water obtained by the distillation can be used again as water for producing subcritical water.

EXAMPLES

The present invention will be described in more detail below by way of Examples thereof.

In each of Examples and Comparative Examples, the thermal decomposition temperature of a thermosetting resin, the glycol recovery percentage, the organic acid recovery percentage, the decomposition percentage and the formation percentage of a compound comprising an acid residue derived from the polyester and a residue derived from the crosslinking moiety (hereinafter referred to as "Compound [1]") were determined as follows.

[Thermal Decomposition Temperature of Thermosetting Resin]

The thermal decomposition temperature was determined as a temperature which corresponded to the intersection point of a tangent drawn at a bending point of the decomposition steps of a resin component on a chart obtained by the thermogravimetric analysis (TG analysis) of a resin sample, with a zero horizontal line of the TG curve.

[Glycol Recovery Percentage]

The glycol recovery percentage was calculated by the following equation:

Glycol recovery percentage(%)=a determined amount of a glycol monomer component/an estimated content of the glycol monomer component in the thermosetting resin×100

[Organic Acid Recovery Percentage]

The organic acid recovery percentage was calculated by the following equation:

Organic acid recover percentage(%)=a determined amount of an organic acid monomer component/ an estimated content of the organic acid monomer component in the thermosetting resin×100

[Decomposition Percentage]

The decomposition percentage was calculated by the following equation:

Decomposition percentage(%)=(the amount of the thermosetting resin–the amount of non-reacted resin residue)/the amount of the thermosetting resin×100

[Formation Percentage of Compound (or Compound [1]) Comprising Acid Residue Derived from Polyester and Residue Derived from Crosslinking Moiety]

The formation percentage of Compound [1] was calculated by the following equation:

Formation percentage(%) of Compound [1]=(the dry weight of a precipitate which was obtained by adding hydrochloric acid to a water-soluble component obtained after the decomposition treatment to thereby adjust the pH thereof at about 4)/(an estimated content of Compound [1] calculated from a ratio between the number of the molecules of an acid residue and the number of the molecules of a residue derived from the crosslinking moiety, obtained by the NMR analysis of a compound obtained by the decomposition, and from the amount of a crosslinking moiety-forming material used)×100

Example 1

A thermosetting resin (an unsaturated polyester resin) for use in a test was prepared. Firstly, vanish was synthesized by mixing propylene glycol (50 wt. %) as a glycol which was a polyhydric alcohol, with maleic anhydride (50 wt. %) which was an unsaturated organic acid. Then, styrene as a crosslinking agent in an amount substantially equivalent to the vanish was mixed thereto. After that, the mixture (50 wt. %) of the vanish and styrene was mixed with calcium carbonate (50 wt. %), and the mixture was cured to obtain the thermosetting resin. The thermal decomposition temperature of the thermosetting resin was 320° C.

Next, the thermosetting resin (3 g) and pure water (15 g) were charged in a reaction tube, and the internal atmosphere of the reaction tube was replaced with an argon gas.

Next, the reaction tube 1 charged with the thermosetting resin and the pure water was immersed in a constant temperature bath 2 of a temperature of 230° C. as shown in FIG. 2, to thereby put the pure water in the reaction tube 1 into a sub-critical state. The reaction tube 1 was left to be immersed in the bath to thereby treat and decompose the thermosetting resin for 4 hours. After that, the reaction tube 1 was removed from the bath 2 and was then immersed in a cooling bath 3 to thereby rapidly cool the reaction tube 1 to room temperature.

The contents in the reaction tube 1 after the decomposition treatment were a water-soluble component, a non-reacted resin residue and calcium carbonate. The contents were filtrated to separate and recover the solid content from the reaction tube 1. Then, the water-soluble component and the non-reacted resin residue were analyzed. The amount of a glycol monomer component was determined from the water-soluble component by gas chromatography (GC analysis), and the glycol recovery percentage was calculated from the result. The amount of an organic acid monomer component was determined by ion exchange chromatography (IC analysis), and the organic acid recovery percentage was calculated from the result. The decomposition percentage was calculated from the non-reacted resin residue. The results are shown in Table 1.

Next, the water-soluble component was neutralized with hydrochloric acid to form a precipitate. Then, the precipitate was recovered and was subjected to a qualitative analysis by way of an infrared spectroscopic analysis (IR analysis) and a nuclear magnetic resonance spectroscopic analysis (NMR analysis). The above precipitate was dried to measure its weight, and the weight of the precipitate was compared with the weight of the thermosetting resin charged in the reaction tube 1, and a calculation was made based on the result of the comparison to find the formation percentage of a compound (Compound [1]) comprising an acid residue derived from the polyester and a residue derived from the crosslinking moiety. The result is shown in Table 1.

Example 2

The decomposition of a thermosetting resin was carried out in the same manner as in Example 1, except that an aqueous KOH solution (KOH concentration: 0.2 mol/l) was used instead of pure water. Also, the glycol recovery percentage, the organic acid recovery percentage, the decomposition percentage and the formation percentage of Compound [1] were calculated in the same manners. The results are shown in Table 1.

Example 3

The decomposition of a thermosetting resin was carried out in the same manner as in Example 1, except that an aqueous KOH solution (KOH concentration: 0.5 mol/l) was used instead of pure water. Also, the glycol recovery percentage, the organic acid recovery percentage, the decomposition percentage and the formation percentage of Compound [1] were calculated in the same manners. The results are shown in Table 1.

Example 4

The decomposition of a thermosetting resin was carried out in the same manner as in Example 1, except that an aqueous KOH solution (KOH concentration: 1.0 mol/l) was used instead of pure water. Also, the glycol recovery percentage, the organic acid recovery percentage, the decomposition percentage and the formation percentage of Compound [1] were calculated in the same manners. The results are shown in Table 1.

Comparative Example 1

The decomposition of a thermosetting resin was carried out in the same manner as in Example 1, except that the reaction tube 1 was immersed in a constant temperature bath 2 of a temperature of 360° C. for 20 minutes, instead of the immersion thereof in the constant temperature bath of a temperature of 230° C. for 4 hours. Also, the glycol recovery percentage, the organic acid recovery percentage, the decomposition percentage and the formation percentage of Compound [1] were calculated in the same manners. The results are shown in Table 1.

Comparative Example 2

The decomposition of a thermosetting resin was carried out in the same manner as in Comparative Example 1, except that an aqueous KOH solution (KOH concentration: 1.0 mol/l) was used instead of pure water. Also, the glycol recovery percentage, the organic acid recovery percentage, the decomposition percentage and the formation percentage of Compound [1] were calculated in the same manners. The results are shown in Table 1.

Comparative Examples 1 and 2, it was needed to use chloroform to separate the water-insoluble component of the decomposition products from the inorganic filler. The chloroform solution of Comparative Example 1 was introduced in a gas chromatograph mass spectrometer to analyze the components of the solution. The results are shown in FIG. 3. As is apparent from the results of the analysis, many components were detected from the solution, and compounds having various structures which could be identified were present therein. It is believed that the thermal decomposition reaction is dominant in the decomposition treatment under these conditions, and therefore, the recovery of useful and high quality substances is hindered.

On the other hand, according to the methods for decomposing plastics in Examples 1 to 3 of the present invention, the thermosetting resins, each comprising a polyester and its crosslinking moiety, were treated with subcritical water of a temperature of 230° C. which is lower than the thermal decomposition temperatures of the thermosetting resins, so that the styrene-fumaric acid copolymers, which were com-

TABLE 1

|  | Ex. 1 | Ex. 2 | Ex. 3 | Ex. 4 | C. Ex. 1 | C. Ex. 2 |
| --- | --- | --- | --- | --- | --- | --- |
| Reaction temp. | 230° C. | 230° C. | 230° C. | 230° C. | 360° C. | 360° C. |
| Pressure | 2.8 MPa | 2.8 MPa | 2.8 MPa | 2.8 MPa | 18.7 MPa | 18.7 MPa |
| Treating time | 4 hrs. | 4 hrs. | 4 hrs. | 4 hrs. | 20 mins. | 20 mins. |
| Base | None | KOH | KOH | KOH | None | KOH |
| Concentration |  | 0.2 mol/l | 0.5 mol/l | 1.0 mol/l |  | 1.0 mol/l |
| Number of moles of alkaline salt to theoretical number of moles of acid residue in Compound [1] | 0 | 1.92 | 4.80 | 9.61 | 0 | 9.61 |
| pH before reaction | 6.59 | 13.18 | 13.35 | 13.65 | 8.3 | 13.50 |
| pH after reaction | 6.87 | 6.58 | 9.83 | 11.50 | 6.3 | 8.9 |
| Decomposition percentage | 5.1% | 36.1% | 86.6% | 100% | 100% | 100% |
| Recovery percentage of glycol | 47.4% | 41.3% | 71.7% | 66.7% | 1.9% | 42.2% |
| Recovery percentage of organic acid | 5.0% | 9.8% | 19.1% | 20.9% | 0.0% | 0.0% |
| Formation percentage of Compound [1] | 1% or less | 1% or less | About 70% | About 80% | 0.1% or less | 0.1% or less |

The glycols and the organic acid monomers recovered in the above Examples were propylene glycols and fumaric acids, respectively. Compounds [1] precipitated by neutralizing the recovered water-soluble components were styrene-fumaric acid copolymers represented by the formula 1:

[Chemical formula 1]

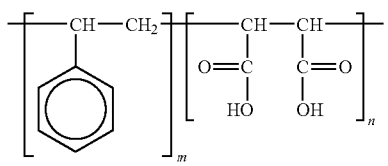

[wherein m and n are integers larger than 1.]

In each of Examples 1 to 3, all of the components obtained after the decomposition treatment of the thermosetting resin with the subcritical water, except for the inorganic filler (calcium carbonate), could be treated with water. In each of pounds (Compounds [1]) each comprising an acid residue derived from the polyester and a residue derived from the crosslinking moiety, could be recovered in addition to glycols and organic acids. Further, as is apparent from Table 1, it was confirmed that the recovery percentages of the glycols and the organic acids of Examples 1 to 3 could be improved by treating the thermosetting resins with the subcritical water of temperatures of 230° C. instead of 360° C., although the treating times of Examples 1 to 3 became longer than those of Comparative Examples 1 and 2.

The invention claimed is:

1. A method for decomposing a plastic, said method comprising:
    treating a thermosetting resin which comprises a polyester and its crosslinking moiety, with subcritical water of a temperature lower than the thermal decomposition temperature of the thermosetting resin; and
    recovering a compound comprising an acid residue derived from the polyester and a residue derived from the crosslinking moiety, obtained from the treating of the thermosetting resin, wherein the subcritical water contains an alkaline salt in an amount of not less than 2 molar equivalents relative to the theoretical number of the moles of an acid residue which is contained in a compound comprising the acid residue derived from the polyester and a residue derived from the crosslinking moiety, obtained by the decomposition of the thermosetting resin.

2. The method according to claim 1, wherein the alkaline salt is a hydroxide of an alkaline metal.

\* \* \* \* \*

UNITED STATES PATENT AND TRADEMARK OFFICE
CERTIFICATE OF CORRECTION

| | |
|---|---|
| PATENT NO. | : 7,601,760 B2 |
| APPLICATION NO. | : 10/593081 |
| DATED | : October 13, 2009 |
| INVENTOR(S) | : Hidaka et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 202 days.

Signed and Sealed this

Fifth Day of October, 2010

David J. Kappos
*Director of the United States Patent and Trademark Office*